United States Patent [19]

Kalnes et al.

[11] Patent Number: 4,899,001

[45] Date of Patent: Feb. 6, 1990

[54] PROCESS FOR THE SIMULTANEOUS HYDROCONVERSION OF A FIRST FEEDSTOCK COMPRISING UNSATURATED, HALOGENATED ORGANIC COMPOUNDS AND A SECOND FEEDSTOCK COMPRISING SATURATED, HALOGENATED ORGANIC COMPOUNDS

[75] Inventors: Tom N. Kalnes, La Grange; Robert B. James, Jr., Northbrook, both of Ill.

[73] Assignee: UOP, Des Plaines, Ill.

[21] Appl. No.: 274,225

[22] Filed: Nov. 21, 1988

[51] Int. Cl.$^4$ ................................................ C10C 1/00
[52] U.S. Cl. ..................................... 585/310; 585/320; 585/469; 585/733; 208/262.5
[58] Field of Search ..................... 208/262.5; 585/310, 585/320, 469, 733

[56] References Cited

U.S. PATENT DOCUMENTS

| | | | |
|---|---|---|---|
| 2,294,699 | 9/1942 | Steffen | 585/310 |
| 3,133,013 | 5/1964 | Watkins | 208/210 |
| 3,592,864 | 7/1971 | Gewartowski | 260/667 |
| 3,595,931 | 7/1971 | Hay et al. | 208/262.5 |

Primary Examiner—Helane Myers
Attorney, Agent, or Firm—Thomas K. McBride; John G. Tolomei; John G. Cutts, Jr.

[57] ABSTRACT

A process for the simultaneous hydroconversion of a first feedstock comprising unsaturated, halogenated organic compounds and a second feedstock comprising saturated, halogenated organic compounds which process comprises: (a) reacting the first feedstock comprising unsaturated, halogenated organic compounds with hydrogen in a first hydrogenation reaction zone operated at hydrogenation conditions selected to minimize the polymerization of unsaturated organic compounds and to produce a first hydrogenated stream comprising hydrocarbonaceous compounds; (b) reacting at least a portion of the first hydrogenated stream comprising hydrocarbonaceous compounds and the second feedstock comprising saturated, halogenated organic compounds with hydrogen in a second hydrogenated reaction zone operated at hydrogenation conditions selected to produce a second hydrogenated stream comprising hydrocarbonaceous compounds and to generate at least one water-soluble inorganic halide compound; (c) contacting the resulting effluent from the second hydrogenation zone containing hydrogenated hydrocarbonaceous compounds and at least one water-soluble inorganic halide compound with a halide-lean aqueous scrubbing solution; and (d) introducing a resulting admixture of the effluent from the second hydrogenation zone and the halide-lean aqueous scrubbing solution into a separation zone to provide a hydrogen-rich gaseous stream, a third hydrogenated stream comprising hydrocarbonaceous compounds and a halide-rich aqueous scrubbing solution containing at least a portion of the water-soluble inorganic halide compound.

12 Claims, 1 Drawing Sheet

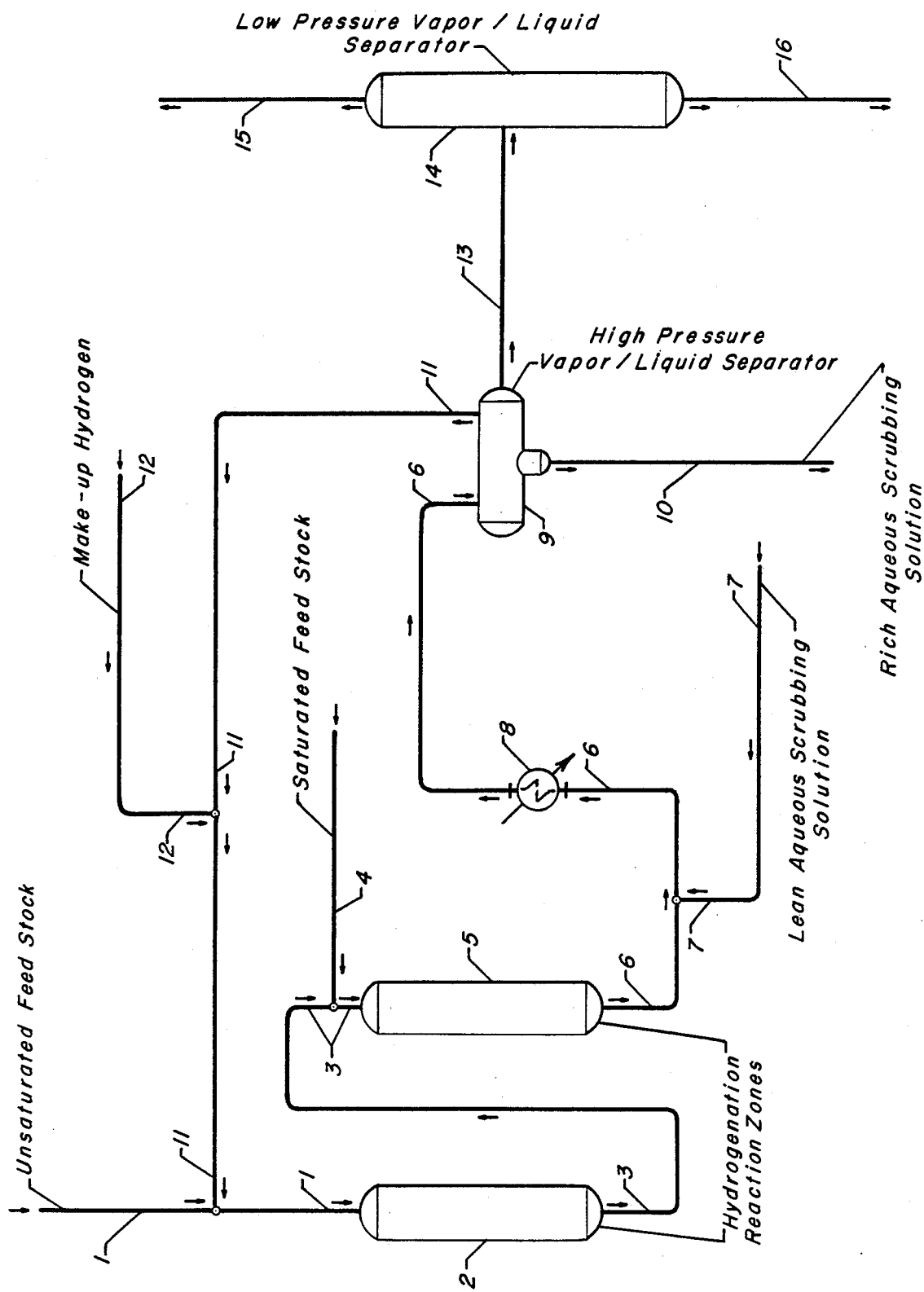

PROCESS FOR THE SIMULTANEOUS HYDROCONVERSION OF A FIRST FEEDSTOCK COMPRISING UNSATURATED, HALOGENATED ORGANIC COMPOUNDS AND A SECOND FEEDSTOCK COMPRISING SATURATED, HALOGENATED ORGANIC COMPOUNDS

BACKGROUND OF THE INVENTION

The field of art to which this invention pertains is the production of a hydrogenated hydrocarbonaceous product from an unsaturated, halogenated organic feed and a saturated, halogenated organic feed.

More specifically, the invention relates to a process for the simultaneous hydroconversion of a first feedstock comprising unsaturated, halogenated organic compounds and a second feedstock comprising saturated, halogenated organic compounds which process comprises: (a) reacting the first feedstock comprising unsturated, halogenated organic compounds with hydrogen in a first hydrogenation reaction zone operated at hydrogenation conditions selected to minimize the polymerization of unsaturated organic compounds and to produce a first hydrogenated stream comprising hydrocarbonaceous compounds; (b) reacting at least a portion of the first hydrogenated stream comprising hydrocarbonaceous compounds and the second feedstock comprising saturated, halogenated organic compounds with hydrogen in a second hydrogenation reaction zone operated at hydrogenation conditions selected to produce a second hydrogenated stream comprising hydrocarbonaceous compounds and to generate at least one water-soluble inorganic halide compound; (c) contacting the resulting effluent from the second hydrogenation zone containing hydrogenated hydrocarbonaceous compounds and at least one water-soluble inorganic halide compound with a halide-lean aqueous scrubbing solution; and (d) introducing a resulting admixture of the effluent from the second hydrogenation zone and the halide-lean aqueous scrubbing solution into a separation zone to provide a hydrogen-rich gaseous stream, a third hydrogenated stream comprising hydrocarbonaceous compounds and a halide-rich aqueous scrubbing solution containing at least a portion of the water-soluble inorganic halide compound.

There is a steadily increasing demand for technology which is capable of the simultaneous hydroconversion of a first feedstock comprising olefinic, halogenated organic compounds and a second feedstock comprising saturated halogenated organic compounds. Previous techniques utilized to dispose of such feedstocks which are often undesirable by-products of other processes such as epichlorohydrin production, for example, have frequently become environmentally unpopular or illegal and, in general, have always been expensive. With the increased environmental emphasis for the treatment and recycle of chlorinated organic products, there is an increased need for the conversion of these products in the event that they become unwanted or undesirable. For example, during the disposal or recycle of potentially environmentally harmful halogenated organic waste streams, an important step in the total solution to the problem is the conditioning of the halogenated organic stream which facilitates the ultimate resolution to provide product streams which may be handled in an environmentally acceptable manner. Therefore, those skilled in the art have sought to find feasible techniques to hydroconvert unsaturated and saturated halogenated organic compounds to provide hydrocarbonaceous product streams which may be safely and usefully employed or recycled. Previous techniques which have been employed include incineration which in addition to potential pollution consideration fails to recover valuable hydrocarbonaceous materials.

INFORMATION DISCLOSURE

In U.S. Pat. No. 3,592,864 (Gewartowski), a process is disclosed for hydrogenating benzene to form cyclohexane utilizing once-through hydrogen-containing gas wherein the exothermic heat of reaction is utilized as the sole source of heat input to steam generation means and wherein the processing system is enhanced by the elimination of recycle gas compressors, treaters, coolers and heaters.

In U.S. Pat. No. 3,133,013 (Watkins), a process is disclosed which relates to the hydro-refining of hydrocarbons for the purpose of removing diverse contaminants therefrom and/or reacting such hydrocarbons to improve the chemical and physical characteristics thereof. In addition, the process is directed toward the selective hydrogenation of unsaturated, coke-forming hydrocarbons through the use of particular conditions whereby the formation of coke, otherwise resulting from the hydrorefining of such hydrocarbon fractions and distillates, is effectively inhibited.

BRIEF SUMMARY OF THE INVENTION

The invention provides an improved process for the production of a hydrogenated hydrocarbonaceous product from an unsaturated, halogenated organic feed and a saturated, halogenated organic feed by means of contacting the unsaturated organic feed in a first hydrogenation reaction zone at hydrogenation conditions selected to saturate the feedstock with hydrogen while minimizing the polymerization of the unsaturated halogenated organic compounds and to contact the effluent from the first hydrogenation zone and the saturated, halogenated organic feed in a second hydrogenation reaction zone at hydrogenation conditions to produce a hydrogenated hydrocarbonaceous product and at least one water-soluble inorganic halide compound. Important elements of the process are the integrated hydrogenation reaction zones which reduce capital and utility costs, and the elimination or at least the minimization of the polymerization of unsaturated halogenated organic compounds which prevents excessive buildup of carbonaceous deposits in the processing equipment and in the catalyst, improves the recovery of inorganic halide compounds and maximizes the quantity of hydrogenated hydrocarbonaceous product.

One embodiment of the invention may be characterized as a process for the simultaneous hydroconversion of a first feedstock comprising unsaturated, halogenated organic compounds and a second feedstock comprising saturated, halogenated organic compounds which process comprises: (a) reacting the first feedstock comprising unsaturated, halogenated organic compounds with hydrogen in a first hydrogenation reaction zone operated at hydrogenation conditions selected to minimize the polymerization of unsaturated organic compounds and to produce a first hydrogenated stream comprising hydrocarbonaceous compounds; (b) reacting at least a portion of the first hydrogenated stream comprising hydrocarbonaceous compounds and the second feedstock comprising saturated, halogenated organic compounds with hydrogen in a second hydrogenation reaction zone operated at hydrogenation conditions selected to produce a second hydrogenated stream comprising hydrocarbonaceous compounds and to generate at least one water-soluble inorganic halide compound; (c) contacting the resulting effluent from the second hydrogenation zone containing hydrogenated hydrocarbonaceous compounds and at least one water-soluble inorganic halide compound with a halide-lean aqueous scrubbing solution; and (d) introducing a resulting admixture of the effluent from the second hydrogenation zone and the halide-lean aqueous scrubbing solution into a separation zone to provide a hydrogen-rich gaseous stream, a third hydrogenated stream comprising hydrocarbonaceous compounds and a halide-rich aqueous scrubbing solution containing at least a portion of the water-soluble inorganic halide compound.

Other embodiments of the present invention encompass further such details such as preferred feedstocks, hydrogenation catalysts, aqueous scrubbing solutions and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved integrated process for the simultaneous hydroconversion of a first feedstock comprising unsaturated, halogenated organic compounds and a second feedstock comprising saturated, halogenated organic compounds. A wide variety of halogenated organic compounds, both unsaturated and saturated, are candidates for feed streams in accordance with the process of the present invention. Examples of organic streams comprising halogenated organic compounds which are suitable for treatment by the process of the present invention are dielectric fluids, hydraulic fluids, heat transfer fluids, used lubricating oil, used cutting oils, used solvents, halogenated hydrocarbonaceous by-products, oils contaminated with polychlorinated biphenyls (PCB), halogenated wastes, petrochemical by-products and other halogenated hydrocarbonaceous industrial wastes. Often, in a particular place or location, two or more halogenated organic streams are present and require further treatment. It has been discovered that unsaturated halogenated organic compounds present a greater challenge for subsequent processing such as hydrogenation as compared with the saturated halogenated organic compounds. When both types of halogenated organic streams are present, they may readily be processed in the integrated hydrogenation process of the present invention. The halogenated organic feed streams which are contemplated for use in the present invention may also contain organic compounds which include sulfur, oxygen, nitrogen or metal components which may be simultaneously hydrogenated to remove or convert such components as desired. The halogenated organic compounds may also contain hydrogen and are therefore then referred to as hydrocarbonaceous compounds.

Preferred feedstocks containing unsaturated, halogenated organic compounds comprise fractionation column bottoms in the production of allyl chloride, fractionation column bottoms in the production of ethylene dichloride, fractionation column bottoms in the production of trichloroethylene and perchloroethylene, used dielectric fluid containing polychlorinated biphenyls (PCB) and chlorinated benzene, used chlorinated solvents, and mixtures thereof.

Preferred feedstocks containing saturated, halogenated organic compounds comprise fractionation bottoms from the purification column in epichlorohydrin production, carbon tetrachloride, 1,1,1 trichloroethane, chlorinated alcohols, chlorinated ethers, chlorofluorocarbons and admixtures thereof.

The halogenated organic compounds which are contemplated as feedstocks in the present invention preferably contain a halogen selected from the group consisting of chlorine and fluorine.

In accordance with the present invention, a feedstock comprising unsaturated, halogenated organic compounds is introduced in admixture with a hydrogen-rich gaseous stream into a catalytic hydrogenation zone containing hydrogenation catalyst and maintained at mild hydrogenation conditions. This catalytic hydrogenation zone may contain a fixed, ebullated or fluidized catalyst bed. This reaction zone is preferably maintained at mild conditions which are chosen to selectively saturate unsaturated organic compounds such as olefins, for example, while simultaneously preventing the formation of polymers or higher molecular weight carbonaceous material. Preferred reaction zone conditions include an imposed pressure from about atmospheric (0 kPa gauge) to about 2,000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 122° F. (50° C.) to about 650° F. (343° C.) selected to perform the desired saturation of unsaturated organic compounds in order to reduce or eliminate the propensity of the unsaturated feed stream to form polymers and gum which are undesirable for further use or processing of the resulting hydrocarbonaceous stream. Although the primary function of this hydrogenation zone is used to saturate the unsaturated halogenated organic charge stream, it is also contemplated in accordance with the present invention that the desired hydrogenation conversion may also include, for example, dehalogenation, desulfurization, denitrification, oxygenate conversion and hydrocracking. Further preferred operating conditions include liquid hourly space velocities in the range from about 0.05 hour$^{-1}$ to about 20 hr$^{-1}$ and hydrogen circulation rates from about 200 standard cubic feet per barrel (SCFB) (33.71 normal m$^3$/m$^3$) to about 100,000 SCFB (16851 normal m$^3$/m$^3$), preferably from about 300 SCFB (50.6 normal m$^3$/m$^3$) to about 50,000 SCFB (8427 normal m$^3$/m$^3$).

The resulting effluent from the first hydrogenation reaction zone which is used to hydrogenate and saturate the unsaturated organic feedstock is admixed with the saturated, halogenated organic feed stream without intermediate separation thereof and the resulting admixture is introduced into a second catalytic hydrogenation zone containing hydrogenation catalyst and maintained at hydrogenation conditions. This second catalytic hydrogenation zone may contain a fixed, ebullated or fluidized catalyst bed. The operating conditions selected for this catalytic hydrogenation zone are selected primarily to dehalogenate the halogenated organic compounds which are introduced thereto and these operating conditions are generally more severe, i.e., promote greater hydrogenation than the operating conditions utilized in the first catalytic hydrogenation zone. This second catalytic hydrogenation zone is preferably maintained under an imposed pressure from about atmospheric (0 kPa gauge) to about 2000 psig (13790 kPa gauge) and more preferably under a pressure from about 100 psig (689.5 kPa gauge) to about 1800 psig (12411 kpa gauge). Suitably, such reaction is conducted with a maximum catalyst bed temperature in the range of about 122° F. (50° C.) to about 850° F. (454° C.) selected to perform the desired hydrogenation and dehalogenation conversion to reduce or eliminate the concentration of halogenated organic compounds contained in the combined feed stream. In accordance with the present invention, it is contemplated that the desired hydrogenation conversion includes, for example, dehalogenation, desulfurization, denitrification, olefin saturation, oxygenate conversion and hydrocracking. Further preferred operating conditions include liquid hourly space velocities in the range from about 0.05 hr.$^{-1}$ to about 20 hr.$^{-1}$ and hydrogen circulation rates from about 200 standard cubic feet per barrel (SCFB) (33.71 normal m$^3$/m$^3$) to about 100,000 SCFB (16851 normal m$^3$/m$^3$), preferably from about 200 SCFB (33.71 normal m$^3$/m$^3$) to about 50,000 SCFB (8427 normal m$^3$/m$^3$).

In the event that the temperature of the combined halogen-containing, organic feed stream which is introduced into the second hydrogenation reaction zone is not deemed to be exactly the temperature selected to operate the second catalytic hydrogenation zone, we contemplate that the temperature of the feed stream to be introduced into the hydrogenation zone may be adjusted either upward or downward in order to achieve the desired temperature in the catalytic hydrogenation zone. Such a temperature adjustment may be accomplished, for example, by either indirect heat exchange or by the addition of either cool or hot hydrogen.

The hydrogen-rich gaseous stream which is recovered from the effluent from the second hydrogenation zone may be recycled to the first and/or the second hydrogenation zone. The first and/or the second hydrogenation zone may contain one or more catalyst zones.

The preferred catalytic composites disposed within the hereinabove described hydrogenation zones can be characterized as containing a metallic component having hydrogenation activity, which component is combined with a suitable refractory inorganic oxide carrier material of either synthetic or natural origin. The precise composition and method of manufacturing the carrier material is not considered essential to the present invention. Preferred carrier materials are alumina, silica, carbon and mixtures thereof. Suitable metallic components having hydrogenation activity are those selected from the group comprising the metals of Groups VI-B and VIII of the Periodic Table, as set forth in the *Periodic Table of the Elements*, E. H. Sargent and Company, 1964. Thus, the catalytic composites may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VI-B are generally present in an amount within the range of from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more of the following components: cesium, francium, lithium, potassium, rubidium, sodium, copper, gold, silver, cadmium, mercury and zinc.

The hydrocarbonaceous effluent from the second hydrogenation zone is preferably contacted with an aqueous scrubbing solution and the admixture is admitted to a separation zone in order to separate a halide-rich aqueous stream, a hydrogenated hydrocarbonaceous liquid phase and a hydrogen-rich gaseous phase. The contact of the hydrocarbonaceous effluent from the second hydrogenation zone with the aqueous scrubbing solution may be performed in any convenient manner and is preferably conducted by co-current, in-line mixing which may be promoted by inherent turbulence, mixing orifices or any other suitable mixing means. The aqueous scrubbing solution is preferably introduced in an amount from about 1 to about 100 volume percent of the total feedstock charged to the second hydrogenation zone based on the composition of the effluent from the second hydrogenation zone. The aqueous scrubbing solution is selected depending on the characteristics of the organic feed stream introduced into the second hydrogenation zone. In accordance with the present invention, at least some halogenated organic compounds are introduced as feedstock and therefore the aqueous scrubbing solution in one embodiment preferably contains a basic compound such as calcium hydroxide, potassium hydroxide or sodium hydroxide in order to neutralize the acid such as hydrogen chloride, hydrogen bromide and hydrogen fluoride, for example, which is formed during the hydrogenation of the halogen compounds. In another preferred embodiment, the halide compound is recovered by dissolution in water or a lean aqueous solution of the halide compound. This embodiment permits the subsequent recovery and use of a desirable and valuable halide compound. The final selection of the aqueous scrubbing solution is dependent upon the particular halide compounds which are present and the desired end product. The resulting hydrogenated hydrocarbonaceous liquid phase is recovered and the hydrogen-rich gaseous phase may be recycled to the hydrogenation zones if desired.

The resulting hydrogenated hydrocarbonaceous liquid phase is preferably recovered from the hydrogen-rich gaseous phase in a separation zone which is maintained at essentially the same pressure as the second hydrogenation reaction zone and as a consequence contains dissolved hydrogen and low molecular weight normally gaseous hydrocarbons if present. In accordance with the present invention, it is preferred that the hydrogenated hydrocarbonaceous liquid phase comprising the hereinabove mentioned gases be stabilized in a convenient manner, such as, for example, by stripping or flashing to remove the normally gaseous components to provide a stable hydrogenated distillable hydrocarbonaceous product. In some cases, we contemplate that a significant portion of the hydrogenated hydrocarbonaceous product may comprise methane, ethane, propane, butane, hexane and admixtures thereof. An adsorbent/stripper arrangement may conveniently be used to recover methane and ethane. Fractionation may conveniently be used to produce purified product streams such as liquid propane or LPG containing propane and butane.

In the drawing, the process of the present invention is illustrated by means of a simplified flow diagram in which such details as total number of reaction zone vessels, pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

With reference now to the drawing, an unsaturated halogenated organic feed stream comprising halogenated organic compounds is introduced into the process via conduit 1 and is contacted with a hydrogen-rich gaseous recycle stream which is provided via conduit 11 and is hereinafter described. The halogenated organic feed stream comprising halogenated organic compounds and the hydrogen-rich gaseous recycle stream are introduced into hydrogenation reaction zone 2. The resulting hydrogenated organic stream is removed from hydrogenation reaction zone 2 via conduit 3, s admixed with a second feed stream comprising saturated, halogenated organic compounds introduced via conduit 4, and is introduced into hydrogenation reaction zone 5 without intermediate separation thereof. The resulting hydrogenated hydrocarbonaceous stream is removed from hydrogenation reaction zone 5 via conduit 6 and is contacted with an aqueous halide-lean alkaline scrubbing solution which is introduced via conduit 7. The resulting admixture of the hydrogenated hydrocarbonaceous effluent and the aqueous alkaline scrubbing solution is passed via conduit 6 and cooled in heat-exchanger 8. The resulting cooled effluent from heat-exchanger 8 is passed via conduit 6 into high pressure vapor/liquid separator 9. A hydrogen-rich gaseous stream is removed from high pressure vapor/liquid separator 9 via conduit 11 and recycled as described hereinabove. Since hydrogen is lost in the process by means of a portion of the hydrogen being dissolved in the exiting liquid hydrocarbon and hydrogen being consumed during the hydrogenation reaction, it is necessary to supplant the hydrogen-rich gaseous stream with make-up hydrogen from some suitable external source, for example, a catalytic reforming unit or a hydrogen plant. Make-up hydrogen may be introduced into the system at any convenient and suitable point, and is introduced in the drawing via conduit 12. A liquid hydrogenated hydrocarbonaceous stream comprising hydrogen in solution is removed from high pressure vapor/liquid separator 9 via conduit 13 and is introduced into low pressure vapor/liquid separator 14. A halide-rich aqueous scrubbing solution is removed from high pressure vapor/liquid separator 9 via conduit 10 and recovered. A gaseous stream comprising hydrogen and any normally gaseous hydrocarbons present is removed from low pressure vapor/liquid separator 14 via conduit 15 and recovered. A normally liquid distillable hydrogenated hydrocarbonaceous product is removed from low pressure vapor/liquid separator 14 via conduit 16 and recovered. In the event that the liquid distillable hydrogenated hydrocarbonaceous product removed via conduit 16 is propane, for example, and is therefore not accurately described as normally liquid, the low pressure vapor/liquid separator 14 may be necessarily operated at a pressure in the range from about 300 psig (2068 kPa gauge) to about 500 psig (3447 kPa gauge). In the event that the feed stream contains water, this water is recovered from high pressure vapor/liquid separator 9 via conduit 10 together with the halide-rich aqueous scrubbing solution as hereinabove described.

The following example is presented for the purpose of further illustrating the process of the present invention, and to indicate the benefits afforded by the utilization thereof in producing a distillable hydrogenated hydrocarbonaceous product.

EXAMPLE

An unsaturated, halogenated organic feedstock having the characteristics presented in Table 1 was charged at a rate of 68 mass units per hour to a first hydrogenation zone containing a palladium on alumina catalyst which was conducted at hydrogenation conditions which included a temperature of 176° F. (80° C.), a pressure of 750 psig (5171 kPa gauge) and a hydrogen circulation rate of 50,000 SCFB (8427 normal m$^3$/m$^3$).

TABLE 1

| Unsaturated, Halogenated Hydrocarbonaceous Feedstock Properties | |
|---|---|
| Specific Gravity @ 60° F. (15° C.) | 1.1955 |
| Distillation, °C. | |
| IBP | 94 |
| 5 | 97 |
| 10 | 98 |
| 50 | 102 |
| 90 | 113 |
| 95 | 130 |
| EP | 134 |
| % Over | 97 |
| % Residue | 3 |
| Composition, Weight Percent | |
| Chlorinated Propenes | 64.7 |
| Chlorinated Propane | 26.8 |
| Chlorinated Alcohols | 0 |
| Chlorinated Ethers | 0 |
| Chlorinated Hexadiene | 0.7 |
| Chlorinated Hexane | — |
| Chlorinated Benzene | 0.2 |
| Other | 7.6 |

The resulting effluent from the first hydrogenation zone and a saturated, halogenated organic feedstock having the characteristics presented in Table 2 in an amount of 102 mass units per hour was charged to a second hydrogenation reaction zone containing a palladium on alumina catalyst which was conducted at hydrogenation conditions which included a temperature of 600° F. (315° C.), a pressure of 750 psig (5171 kPa gauge) and a hydrogen circulation rate of 25,000 SCFB (4213 normal m$^3$/m$^3$).

TABLE 2

| Saturated, Halogenated Hydrocarbonaceous Feedstock Properties | |
|---|---|
| Specific Gravity @ 60° F. (15° C.) | 1.3824 |
| Distillation, °C. | |
| IBP | 96 |
| 5 | 119 |
| 10 | 132 |
| 50 | 156 |
| 90 | 252 |
| 95 | 258 |
| EP | 259 |
| % Over | 96 |
| % Residue | 4 |
| Composition, Weight Percent | |
| Chlorinated Propenes | — |

TABLE 2-continued

| Saturated, Halogenated Hydrocarbonaceous Feedstock Properties | |
| --- | --- |
| Chlorinated Propane | 49.8 |
| Chlorinated Alcohols | 12.1 |
| Chlorinated Ethers | 31.1 |
| Chlorinated Hexadiene | — |
| Chlorinated Hexane | 3.4 |
| Chlorinated Benzene | — |
| Other | 3.6 |

The resulting effluent from the second hydrogenation reaction zone was neutralized with an aqueous solution containing potassium hydroxide and was found to contain 38 mass units of hydrocarbonaceous products having the characteristics presented in Table 3.

TABLE 3

| Hydrocarbonaceous Product Stream Properties | |
| --- | --- |
| Composition, Weight Percent | |
| Ethane | 0.3 |
| Propane | 96.6 |
| Chlorinated Propane | Trace |
| Butane | Trace |
| Pentane | 0.0 |
| Hexane and Nonane | 3.1 |
| | 100.0 |

The foregoing description, drawing and example clearly illustrate the advantages encompassed by the process of the present invention and the benefits to be afforded with the use thereof.

What is claimed:

1. A process for the simultaneous hydrodehalogenation of a first feedstock comprising unsaturated, halogenated organic compounds and a second feedstock comprising saturated, halogenated organic compounds which process comprises:
   (a) reacting said first feedstock comprising unsaturated, halogenated organic compounds with hydrogen in a first hydrogenation reaction zone operated at hydrogenation conditions selected to minimize the polymerization of unsaturated organic compounds and to produce a first hydrogenated stream comprising hydrocarbonaceous compounds;
   (b) reacting at least a portion of said first hydrogenated stream comprising hydrocarbonaceous compounds and said second feedstock comprising saturated, halogenated organic compounds with hydrogen in a second hydrogenation reaction zone operated at hydrogenation conditions selected to produce a second hydrogenated stream comprising hydrocarbonaceous compounds and to generate at least one water-soluble inorganic halide compound;
   (c) contacting the resulting effluent from said second hydrogenation zone containing hydrogenated hydrocarbonaceous compounds and at least one water-soluble inorganic halide compound with a halide-lean aqueous scrubbing solution; and
   (d) introducing a resulting admixture of said effluent from said second hydrogenation zone and said halide-lean aqueous scrubbing solution into a separation zone to provide a hydrogen-rich gaseous stream, a third hydrogen-ated stream comprising hydrocarbonaceous compounds and a halide-rich aqueous scrubbing solution containing at least a portion of said water-soluble inorganic halide compound.

2. The process of claim 1 wherein at least a portion of said hydrogen-rich gaseous stream recovered in step (d) is recycled to step (a).

3. The process of claim 1 wherein at least a portion of said hydrogen-rich gaseous stream recovered in step (d) is recycled to step (b).

4. The process of claim 1 wherein said first feedstock comprising unsaturated, halogenated organic compounds comprises fractionation column bottoms in the production of allyl chloride, fractionation column bottoms in the production of ethylene dichloride, fractionation column bottoms in the production of trichloroethylene and perchloroethylene, used dielectric fluid containing polychlorinated biphenyls (PCB) and chlorinated benzene, used chlorinated solvents, and mixtures thereof.

5. The process of claim 1 wherein said second feedstock comprising saturated, halogenated organic compounds comprises fractionation bottoms from the purification column in epichlorohydrin production, carbon tetrachloride, 1,1,1 trichloroethane, chlorinated alcohols, chlorinated ethers, chlorofluorocarbons and admixtures thereof.

6. The process of claim 1 wherein said first hydrogenation reaction zone comprises at least two catalyst zones.

7. The process of claim 1 wherein said second hydrogenation reaction zone comprises at least two catalyst zones.

8. The process of claim 1 wherein the effluent from said second hydrogenation zone containing said water-soluble inorganic halide compound is contacted with an aqueous solution to recover said water-soluble inorganic halide compound.

9. The process of claim 1 wherein said first hydrogenation reaction zone is operated at conditions which include a pressure from about atmospheric (0 kPa gauge) to about 2000 psig (13790 kpa gauge), a maximum catalyst temperature from about 122° F. (50° C.) to about 650° F. (343° C.) and a hydrogen circulation from about 200 SCFB (33.7 normal m$^3$/m$^3$) to about 100,000 SCFB (16851 normal m$^3$/m$^3$).

10. The process of claim 1 wherein said second hydrogenation reaction zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (33.7 normal m$^3$/m$^3$) to about 50,000 SCFB (8427 normal m$^3$/m$^3$).

11. The process of claim 1 wherein said halogenated organic compounds contain a halogen selected from the group consisting of chlorine and fluorine.

12. The process of claim 1 wherein said water-soluble inorganic halide compound is selected from the group consisting of hydrogen chloride and hydrogen fluoride.

* * * * *